(12) United States Patent
Brynjelsen et al.

(10) Patent No.: US 9,517,269 B1
(45) Date of Patent: Dec. 13, 2016

(54) STABLE PENTOBARBITAL FORMULATION

(71) Applicant: Akorn, Inc., Lake Forest, IL (US)

(72) Inventors: Sean E. Brynjelsen, Barrington, IL (US); Biswajit Pati, Buffalo Grove, IL (US)

(73) Assignee: Akorn, Inc., Lake Forest, IL (US)

(*) Notice: Subject to any disclaimer, the term of this patent is extended or adjusted under 35 U.S.C. 154(b) by 0 days.

(21) Appl. No.: 14/617,404

(22) Filed: Feb. 9, 2015

Related U.S. Application Data

(63) Continuation of application No. 14/046,524, filed on Oct. 4, 2013, now abandoned, which is a continuation of application No. 14/043,467, filed on Oct. 1, 2013, now abandoned.

(51) Int. Cl.
*A61K 47/10* (2006.01)
*A61K 31/515* (2006.01)

(52) U.S. Cl.
CPC .............. *A61K 47/10* (2013.01); *A61K 31/515* (2013.01)

(58) Field of Classification Search
CPC .............................. A61K 47/10; A61K 31/515
See application file for complete search history.

(56) References Cited

PUBLICATIONS https://web.archive.org/web/20110613034838/http://www.rxlist.com/nembutal-drug.htm (Date from Wayback Machine Jun. 13, 2011).*

* cited by examiner

*Primary Examiner* — Sahar Javanmard
(74) *Attorney, Agent, or Firm* — Polsinelli PC; Ron Galant

(57) ABSTRACT

The present invention relates to a pentobarbital formulation with greater stability and fewer impurities. In particular, the formulation may be an aqueous formulation containing 50 mg/mL pentobarbital sodium, 50% glycol, and 10% alcohol, at a pH of 9.4.

4 Claims, 8 Drawing Sheets

Figure 1

LOT NUMBER: 041143 IAC
PRODUCT NAME: Pentobarbital Sodium Injection USP 50mg/mL
FORMULA #: 686
FILL DATE: 04/03/2013
DATE ON STABILITY: 04/08/2013

REASON FOR STABILITY: ANDA submission exhibit batch
SAMPLE ORIENTATION: Inverted
ACTIVE MATERIAL: Pentobarbital Sodium -- Siegfried
CONTAINER: Kimble 50cc clear vial
CLOSURE: 20mm Omniflex Plus FM259/0 stopper
EXPIRATION DATE: 04/2016

STORAGE CONDITION: ACC (38°C-42°C 75 +/-5%RH)

| Test | Specification Acceptance Criteria | Method | 0 MONTH | 1 MONTH | 2 MONTHS | 3 MONTHS |
|---|---|---|---|---|---|---|
| Pentobarbital Sodium | 92.0% - 108.0% | ATM253 | 100.4 | 99.2 | 98.1 | 100.2 |
| Pentobarbital Related Compound 1 RRT 0.7 | Not More Than 1.0% | ATM252 | LT 0.1 | 0.2 | 0.4 | 0.6 |
| Largest Unidentified Individual Related Compound | Not More Than 0.2% | ATM252 | LT 0.1 | LT 0.1 | LT 0.1 | LT 0.1 |
| Total Related Compounds | Not More Than 1.5% | ATM252 | 0.1 | 0.3 | 0.5 | 0.7 |
| Ethyl Alcohol | 8.5% - 11.0% | ATM269 | 10 | 9.0 | 8.5 | 8.5 |
| Product Appearance | Clear, colorless solution | VISUAL | CONFORMS | CONFORMS | CONFORMS | CONFORMS |
| Container Appearance | No visible deterioration | VISUAL | CONFORMS | CONFORMS | CONFORMS | CONFORMS |
| pH | 9.0 - 10.5 | QC204 | 9.5 | 9.4 | 9.4 | 9.4 |
| Visual Particulate Matter | Essentially particle free | RD016 | CONFORMS | CONFORMS | CONFORMS | CONFORMS |
| Color of Solution | Solution Colorless | ATM320 | CONFORMS | CONFORMS | CONFORMS | CONFORMS |
| Clarity of Solution | Solution clear and no visible particles | ATM319 | CONFORMS | CONFORMS | CONFORMS | CONFORMS |
| Container Closure Integrity | Conforms (Integral) | RD125 | N/A | N/A | N/A | CONFORMS |
| Bacterial Endotoxin | Conforms (NMT 0.58 EU/mg) | ML114 | LT 0.12 | N/A | N/A | LT 0.12 |
| USP Sterility Test | Sterile | MTM004 | STERILE | N/A | N/A | STERILE |
| 10 um Particulate Matter | NMT 6000 particles/container | ML115 | 63 | N/A | N/A | 77 |
| 25 um Particulate Matter | NMT 600 particles/container | ML115 | 50 | N/A | N/A | 67 |
| Oxygen Headspace | For Information Only | QC218 | 5.9 | 5.4 | 5.3 | 5.9 |

Figure 2

LOT NUMBER: 041143.ILT
PRODUCT NAME: Pentobarbital Sodium Injection USP 50mg/mL
FORMULA #: 686
FILL DATE: 04/03/2013
DATE ON STABILITY: 04/08/2013

REASON FOR STABILITY: ANDA submission exhibit batch
SAMPLE ORIENTATION: Inverted
ACTIVE MATERIAL: Pentobarbital Sodium – Siegfried
CONTAINER: Kimble 50cc clear vial
CLOSURE: 20mm Omniflex Plus FM259/0 stopper
EXPIRATION DATE: 04/2016

STORAGE CONDITION: LTT (23°C-27°C 60 +/-5%RH)

| Test | Specification Acceptance Criteria | Method | 0 MONTH | 1 MONTH | 3 MONTHS |
|---|---|---|---|---|---|
| Pentobarbital Sodium | 92.0% - 108.0% | ATM253 | 100.4 | 100.4 | 98.7 |
| Pentobarbital Related Compound 1 RRT 0.7 | Not More Than 1.0% | ATM252 | LT 0.1 | LT 0.1 | 0.1 |
| Largest Unidentified Individual Related Compound | Not More Than 0.2% | ATM252 | LT 0.1 | LT 0.1 | LT 0.1 |
| Total Related Compounds | Not More Than 1.5% | ATM252 | 0.1 | 0.1 | 0.2 |
| Ethyl Alcohol | 8.5% TO 11.0% | ATM269 | 10 | 10 | 8.5 |
| Product Appearance | Clear, colorless solution | VISUAL | CONFORMS | CONFORMS | CONFORMS |
| Container Appearance | No visible deterioration | VISUAL | CONFORMS | CONFORMS | CONFORMS |
| pH | 9.0 - 10.5 | QC204 | 9.5 | 9.5 | 9.4 |
| Visual Particulate Matter | Essentially particle free | RD016 | CONFORMS | CONFORMS | CONFORMS |
| Color of Solution | Solution Colorless | ATM320 | CONFORMS | CONFORMS | CONFORMS |
| Container Closure Integrity | Conforms (Integral) | RD125 | N/A | N/A | N/A |
| Clarity of Solution | Solution clear and no visible particles | ATM319 | CONFORMS | CONFORMS | CONFORMS |
| Bacterial Endotoxin | Conforms (NMT 0.58 EU/mg) | ML114 | LT 0.12 | LT 0.12 | N/A |
| USP Sterility Test | Sterile | MTM004 | STERILE | STERILE | N/A |
| 10 um Particulate Matter | NMT 6000 particles/container | ML115 | 63 | 63 | N/A |
| 25 um Particulate Matter | NMT 600 particles/container | ML115 | 50 | 50 | N/A |
| Oxygen Headspace | For information only | QC218 | 5.9 | 5.9 | 5.3 |

Figure 3

LOT NUMBER: 041143.UAC
PRODUCT NAME: Pentobarbital Sodium Injection USP 50mg/mL
FORMULA #: 686
FILL DATE: 04/03/2013
DATE ON STABILITY: 04/08/2013

REASON FOR STABILITY: ANDA submission exhibit batch
SAMPLE ORIENTATION: Upright
ACTIVE MATERIAL: Pentobarbital Sodium -- Siegfried
CONTAINER: Kimble 50cc clear vial
CLOSURE: 20mm Omniflex Plus FM259/0 stopper
EXPIRATION DATE: 04/2016

STORAGE CONDITION: ACC (38°C-42°C 75 +/-5%RH)

| Test | Specification Acceptance Criteria | Method | 0 MONTH | 3 MONTHS | SAMPLE AGE | | | |
|---|---|---|---|---|---|---|---|---|
| Pentobarbital Sodium | 92.0% - 108.0% | RD348 | 100.4 | 97.5 | | | | |
| Pentobarbital Related Compound 1 RRT 0.7 | Not More Than 1.0% | ATM252 | LT 0.1 | 0.6 | | | | |
| Largest Unidentified Individual Related Compound | NMT 0.2% | ATM252 | LT 0.1 | LT 0.1 | | | | |
| Total Related Compounds | Not More Than 1.5% | RD348 | 0.1 | 0.7 | | | | |
| Ethyl Alcohol | 8.5% TO 11.0% | ATM269 | 10 | 8.5 | | | | |
| Color of Solution | Solution colorless | ATM320 | CONFORMS | CONFORMS | | | | |
| Clarity of Solution | Solution clear and no visible particles | ATM319 | CONFORMS | CONFORMS | | | | |
| Product Appearance | Clear, colorless solution | VISUAL | CONFORMS | CONFORMS | | | | |
| Container Appearance | No visible deterioration | VISUAL | CONFORMS | CONFORMS | | | | |
| pH | 9.0 - 10.5 | QC204 | 9.5 | 9.4 | | | | |
| Visual Particulate Matter | Essentially particle free | RD016 | CONFORMS | CONFORMS | | | | |
| Oxygen Headspace | For information only | QC218 | 5.9 | 6.2 | | | | |

Figure 4

LOT NUMBER: 041143.ULT
PRODUCT NAME: Pentobarbital Sodium Injection USP 50mg/mL
FORMULA #: 686
FILL DATE: 04/03/2013
DATE ON STABILITY: 04/08/2013

REASON FOR STABILITY: ANDA submission exhibit batch
SAMPLE ORIENTATION: Upright
ACTIVE MATERIAL: Pentobarbital Sodium -- Siegfried
CONTAINER: Kimble 50cc clear vial
CLOSURE: 20mm Omniflex Plus FM259/0 stopper
EXPIRATION DATE: 04/2016

STORAGE CONDITION: LTT (23°C-27°C 60 +/-5%RH)

| Test | Specification Acceptance Criteria | Method | SAMPLE AGE | | |
|---|---|---|---|---|---|
| | | | 1 MONTH | 3 MONTHS | |
| Pentobarbital Sodium | 92.0% - 108.0% | RD348 | 100.4 | 99.5 | |
| Pentobarbital Related Compound 1 RRT 0.7 | Not More Than 2.0% | ATM252 | LT 0.1 | 0.1 | |
| Largest Unidentified Individual Related Compound | Not More Than 0.2% | ATM252 | LT 0.1 | LT 0.1 | |
| Total Related Compounds | Not More Than 2.5% | ATM252 | 0.1 | 0.2 | |
| Ethyl Alcohol | 8.5% TO 11.0% | ATM269 | 10 | 9.0 | |
| Color of Solution | Solution colorless | ATM320 | CONFORMS | CONFORMS | |
| Clarity of Solution | Solution clear and no visible particles | ATM319 | CONFORMS | CONFORMS | |
| Product Appearance | Clear, colorless solution | VISUAL | CONFORMS | CONFORMS | |
| Container Appearance | No visible deterioration | VISUAL | CONFORMS | CONFORMS | |
| pH | 9.0 - 10.5 | QC204 | 9.5 | 9.4 | |
| Visual Particulate Matter | Essentially particle free | RD016 | CONFORMS | CONFORMS | |
| Oxygen Headspace | For information only | QC218 | 5.9 | 5.5 | |

Figure 5

LOT NUMBER: 041173.1AC
PRODUCT NAME: Pentobarbital Sodium Injection USP 50mg/mL
FORMULA #: 688
FILL DATE: 04/05/2013
DATE ON STABILITY: 04/08/2013

REASON FOR STABILITY: ANDA submission exhibit batch
SAMPLE ORIENTATION: Inverted
ACTIVE MATERIAL: Pentobarbital Sodium -- Siegfried
CONTAINER: Kimble 20cc clear vial
CLOSURE: 20mm Omniflex Plus FM259/0 stopper
EXPIRATION DATE: 04/2016

STORAGE CONDITION: ACC (38°C-42°C 75 +/-5%RH)

| Test | Specification Acceptance Criteria | Method | 0 MONTH | 1 MONTH | SAMPLE AGE 2 MONTHS | 3 MONTHS |
|---|---|---|---|---|---|---|
| Pentobarbital Sodium | 92.0% - 108.0% | ATM253 | 99.9 | 99.4 | 99.2 | 98.6 |
| Pentobarbital Related Compound 1 RRT 0.7 | Not More Than 1.0% | ATM252 | LT 0.1 | 0.2 | 0.4 | 0.6 |
| Largest Unidentified Individual Related Compound | Not More Than 0.2% | ATM252 | LT 0.1 | LT 0.1 | NONE DETECTED | LT 0.1 |
| Total Related Compounds | Not More Than 1.5% | ATM252 | 0.1 | 0.3 | 0.5 | 0.7 |
| Ethyl Alcohol | 8.5% - 11.0% | ATM269 | 10 | 8.5 | 8.5 | 9.0 |
| Product Appearance | Clear, colorless solution | VISUAL | CONFORMS | CONFORMS | CONFORMS | CONFORMS |
| Container Appearance | No visible deterioration | VISUAL | CONFORMS | CONFORMS | CONFORMS | CONFORMS |
| pH | 9.0 - 10.5 | QC204 | 9.5 | 9.4 | 9.4 | 9.4 |
| Visual Particulate Matter | Essentially particle free | RD016 | CONFORMS | CONFORMS | CONFORMS | CONFORMS |
| Color of Solution | Solution Colorless | ATM320 | CONFORMS | CONFORMS | CONFORMS | CONFORMS |
| Clarity of Solution | Solution clear and no visible particles | ATM319 | CONFORMS | CONFORMS | CONFORMS | CONFORMS |
| Container Closure Integrity | Conforms (Integral) | RD125 | N/A | N/A | N/A | CONFORMS |
| Bacterial Endotoxin | Conforms (NMT 0.58 EU/mg) | ML114 | LT 0.12 | N/A | N/A | LT 0.12 |
| USP Sterility Test | Sterile | MTM004 | STERILE | N/A | N/A | STERILE |
| 10 um Particulate Matter | NMT 6000 particles/container | ML115 | 24 | N/A | N/A | 292 |
| 25 um Particulate Matter | NMT 600 particles/container | ML115 | 7 | N/A | N/A | 268 |
| Oxygen Headspace | For Information Only | QC218 | 6.1 | 6.0 | 6.6 | 6.7 |

Figure 6

LOT NUMBER: 041173 ILT
PRODUCT NAME: Pentobarbital Sodium Injection USP 50mg/mL
FORMULA #: 688
FILL DATE: 04/05/2013
DATE ON STABILITY: 04/08/2013

REASON FOR STABILITY: ANDA submission exhibit batch
SAMPLE ORIENTATION: Inverted
ACTIVE MATERIAL: Pentobarbital Sodium – Siegfried
CONTAINER: Kimble 20cc clear vial
CLOSURE: 20mm Omniflex Plus FM259/0 stopper
EXPIRATION DATE: 04/2016

STORAGE CONDITION: LTT (23°C-27°C 60 +/-5%RH)

| Test | Specification Acceptance Criteria | Method | 0 MONTH | 1 MONTH | 3 MONTHS | SAMPLE AGE | | | | | | | |
|---|---|---|---|---|---|---|---|---|---|---|---|---|---|
| Pentobarbital Sodium | 92.0% - 108.0% | ATM253 | 99.9 | | 99.7 | | | | | | | | |
| Largest Unidentified Individual Related Compound | Not More Than 0.2% | ATM252 | LT 0.1 | | LT 0.1 | | | | | | | | |
| Pentobarbital Related Compound 1 RRT 0.7 | Not More Than 2.0% | ATM252 | LT 0.1 | | 0.1 | | | | | | | | |
| Total Related Compounds | Not More Than 2.5% | ATM252 | 0.1 | | 0.2 | | | | | | | | |
| Ethyl Alcohol | 8.5% TO 11.0% | ATM269 | 10 | | 9.0 | | | | | | | | |
| Product Appearance | Clear, colorless solution | VISUAL | CONFORMS | | CONFORMS | | | | | | | | |
| Container Appearance | No visible deterioration | VISUAL | CONFORMS | | CONFORMS | | | | | | | | |
| pH | 9.0 - 10.5 | QC204 | 9.5 | | 9.4 | | | | | | | | |
| Visual Particulate Matter | Essentially particle free | RD016 | CONFORMS | | CONFORMS | | | | | | | | |
| Color of Solution | Solution colorless | ATM320 | CONFORMS | | CONFORMS | | | | | | | | |
| Clarity of Solution | Solution clear and no visible particles | ATM319 | CONFORMS | | CONFORMS | | | | | | | | |
| Container Closure Integrity | Conforms (Integral) | RD125 | N/A | | N/A | | | | | | | | |
| Bacterial Endotoxin | Conforms (NMT 0.58 EU/mg) | ML114 | LT 0.12 | | N/A | | | | | | | | |
| USP Sterility Test | Sterile | MTM004 | STERILE | | N/A | | | | | | | | |
| 10 um Particulate Matter | NMT 6000 particles/container | ML115 | 24 | | N/A | | | | | | | | |
| 25 um Particulate Matter | NMT 600 particles/container | ML115 | 7 | | N/A | | | | | | | | |
| Oxygen Headspace | For information only | QC218 | 6.1 | | 7.4 | | | | | | | | |

Figure 7

LOT NUMBER: 041173.UAC
PRODUCT NAME: Pentobarbital Sodium Injection USP 50mg/mL
FORMULA #: 688
FILL DATE: 04/05/2013
DATE ON STABILITY: 04/08/2013

REASON FOR STABILITY: ANDA submission exhibit batch
SAMPLE ORIENTATION: Upright
ACTIVE MATERIAL: Pentobarbital Sodium -- Siegfried
CONTAINER: Kimble 20cc clear vial
CLOSURE: 20mm Omniflex Plus FM259/0 stopper
EXPIRATION DATE: 04/2016

STORAGE CONDITION: ACC (38°C-42°C 75 +/-5%RH)

| Test | Specification Acceptance Criteria | Method | 0 MONTH | 3 MONTHS | SAMPLE AGE | | | | | |
|---|---|---|---|---|---|---|---|---|---|---|
| Pentobarbital Sodium | 92.0% - 108.0% | ATM253 | 99.9 | 100.9 | | | | | | |
| Pentobarbital Related Compound 1 RRT 0.7 | Not More Than 1.0% | ATM252 | LT 0.1 | 0.6 | | | | | | |
| Largest Unidentified Individual Related Compound | Not More Than 0.2% | ATM253 | LT 0.1 | LT 0.1 | | | | | | |
| Total Related Compounds | Not More Than 1.5% | ATM253 | 0.1 | 0.7 | | | | | | |
| Ethyl Alcohol | 8.5% - 11.0% | ATM269 | 10 | 8.5 | | | | | | |
| Product Appearance | Clear, colorless solution | VISUAL | CONFORMS | CONFORMS | | | | | | |
| Container Appearance | No visible deterioration | VISUAL | CONFORMS | CONFORMS | | | | | | |
| pH | 9.0 - 10.5 | QC204 | 9.5 | 9.4 | | | | | | |
| Visual Particulate Matter | Essentially particle free | RD016 | CONFORMS | CONFORMS | | | | | | |
| Color of Solution | Solution colorless | ATM320 | CONFORMS | CONFORMS | | | | | | |
| Clarity of Solution | Solution clear and no visible particles | ATM319 | CONFORMS | CONFORMS | | | | | | |
| Oxygen Headspace | For information only | QC218 | 6.1 | 6.9 | | | | | | |

Figure 8

LOT NUMBER: 041173.ULT
PRODUCT NAME: Pentobarbital Sodium Injection USP 50mg/mL
FORMULA #: 688
FILL DATE: 04/05/2013
DATE ON STABILITY: 04/08/2013

REASON FOR STABILITY: ANDA submission exhibit batch
SAMPLE ORIENTATION: Upright
ACTIVE MATERIAL: Pentobarbital Sodium -- Siegfried
CONTAINER: Kimble 20cc clear vial
CLOSURE: 20mm Omniflex Plus FM259/0 stopper
EXPIRATION DATE: 04/2016

STORAGE CONDITION: LTT (23°C-27°C 60 +/-5%RH)

| Test | Specification Acceptance Criteria | Method | 0 MONTH | 3 MONTHS | SAMPLE AGE | | |
|---|---|---|---|---|---|---|---|
| Pentobarbital Sodium | 92.0% – 108.0% | ATM253 | 99.9 | 99.5 | | | |
| Pentobarbital Related Compound 1 RRT 0.7 | Not More Than 1.0% | ATM252 | LT 0.1 | 0.1 | | | |
| Largest Unidentified Individual Related Compound | Not More Than 0.2% | ATM252 | LT 0.1 | LT 0.1 | | | |
| Total Related Compounds | Not More Than 1.5% | ATM252 | 0.1 | 0.2 | | | |
| Ethyl Alcohol | 8.5% TO 11.0% | ATM269 | 10 | 8.5 | | | |
| Product Appearance | Clear, colorless solution | VISUAL | CONFORMS | CONFORMS | | | |
| Container Appearance | No visible deterioration | VISUAL | CONFORMS | CONFORMS | | | |
| pH | 9.0 – 10.5 | QC204 | 9.5 | 9.4 | | | |
| Visual Particulate Matter | Essentially particle free | RD016 | CONFORMS | CONFORMS | | | |
| Color of Solution | Solution colorless | ATM320 | CONFORMS | CONFORMS | | | |
| Clarity of Solution | Solution clear and no visible particles | ATM319 | CONFORMS | CONFORMS | | | |
| Oxygen Headspace | For information only | QC218 | 6.1 | 7.7 | | | |

STABLE PENTOBARBITAL FORMULATION

FIELD OF THE INVENTION

The present invention relates to a stable formulation of pentobarbital.

BACKGROUND OF THE INVENTION

Pentobarbital (5-Ethyl-5-(1-methylbutyl)-2,4,6(1H,3H,5H)-pyrimidinetrione) is a barbiturate with the following structure

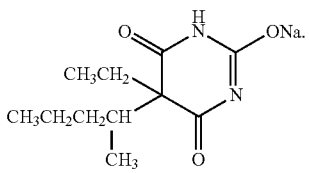

It is used as a sedative, a hypnotic for short term treatment of insomnia, a preanesthetic, and as an anticonvulsant in the emergency control of acute convulsive episodes. The drug can be administered intravenously or intramuscularly. A typical dose for pentobarbital sodium is 50 mg/mL. Common formulations of pentobarbital sodium injection include 40% propylene glycol and 10-15% alcohol. The recommended formulation pH range is 9.0-10.5.

Even within the recommended range of pH levels, the pH of pentobarbital formulations, like those of marketed formulations, can be problematic. On one hand, at a pH less than 9.0, pentobarbital precipitates. On the other, at high pH values greater than 9.0 that are typically necessary to keep pentobarbital in solution, the drug degrades over time via hydrolysis. Depending on their levels, the drug degradation products may affect drug potency or have toxicological effects. One primary degradation product involves a base-catalyzed ring opening of the ring in the pentobarbital molecule, as shown in the following reaction.

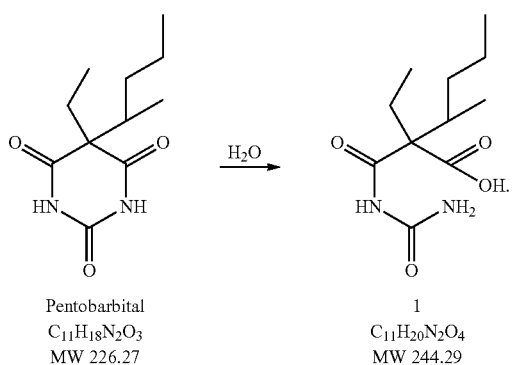 [SMILES: CCCC(C)C1(CC)C(=O)NC(=O)NC1=O ; O ; CCCC(C)C(CC)(C(=O)O)C(=O)NC(N)=O]

Pentobarbital
$C_{11}H_{18}N_2O_3$
MW 226.27

1
$C_{11}H_{20}N_2O_4$
MW 244.29

The degradation product (labeled "1" above and also called "Impurity 1" or "Related Compound 1") accumulates to more than 1% of the active ingredient concentration before the end of three-year marketed drug formulation shelf life. Although the degradation is caused by high pH, even reducing the pH to 8.5 in a pentobarbital formulation containing 40% propylene glycol and 15% alcohol, failed to sufficiently stabilize pentobarbital. As a result, there is a need in the art to provide a pentobarbital formulation with greater stability and a lower impurity levels.

SUMMARY OF THE INVENTION

Provided herein is a composition comprising a pentobarbital, a glycol, an alcohol, and water. The glycol concentration may be 40-60% (v/v) or 50% (v/v). The glycol may be ethylene glycol, propylene glycol or diethylene glycol. The alcohol concentration may be 10-20% (v/v) or may be 10% (v/v). The alcohol may be ethanol, benzyl alcohol or isopropyl alcohol. The pentobarbital concentration may be 50 mg/mL. The pentobarbital may be a sodium or calcium salt of pentobarbital. The pH of the composition may be 8.5-10.5, or may be 9.4. Also provided herein is a composition comprising water, 50 mg/mL pentobarbital sodium, 50% (v/v) propylene glycol, and 10% (v/v) alcohol, wherein the pH of the composition is 9.4.

BRIEF DESCRIPTION OF THE DRAWINGS

FIGS. 1-8 show the results of stability testing for a 50 mg/mL pentobarbital formulation containing 50% propylene glycol and 10% ethanol, at a pH of 9.4.

FIG. 1 shows data from a 50 mL vial of the formulation, tested at 38-40° C., 75% relative humidity, with the sample inverted.

FIG. 2 shows the data from a 50 mL vial of the formulation, tested at 23-27° C., 60% relative humidity, with the sample inverted.

FIG. 3 shows the data from a 50 mL vial of the formulation, tested at 38-42° C., 75% relative humidity, with the sample upright.

FIG. 4 shows the data from a 50 mL vial of the formulation, tested at 23-27° C., 60% relative humidity, with the sample upright.

FIG. 5 shows the data from a 20 mL vial of the formulation, tested at 38-42° C., 75% relative humidity, with the sample inverted.

FIG. 6 shows the data from a 20 mL vial of the formulation, tested at 23-27° C., 60% relative humidity, with the sample inverted.

FIG. 7 shows the data from a 20 mL vial of the formulation, tested at 38-42° C., 75% relative humidity, with the sample upright.

FIG. 8 shows the data from 20 mL vial of the formulation, tested at 23-27° C., 60% relative humidity, with the sample upright.

DETAILED DESCRIPTION

The inventors have discovered that a pentobarbital formulation containing certain concentrations of propylene glycol and alcohol, and a certain pH, provides a surprising degree of stability for pentobarbital. This is despite many attempts by others in the prior art to prevent the active ingredient from degrading, while maintaining a pH that is capable of preventing pentobarbital from precipitating. The formulation described herein accumulates impurities such as Impurity 1 at a lower rate than other formulations described in the prior art. Accordingly, the formulation described herein may be less toxic than prior art formulations.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

2. Pentobarbital Formulation

Provided herein is a composition, which may comprise pentobarbital, water, a glycol, and an alcohol. The composition may be sterile. The composition may also comprise an acid and/or a base, which may be used to adjust the pH of the composition. The acid may be hydrochloric acid and the base may be sodium hydroxide. The composition may further comprise an antioxidant, which may be butylated hyroxytoluene (BHT) or sodium sulfite. The composition may be pharmaceutically acceptable.

a. pH

The pH of the composition may be within a range with an upper limit of 9.0, 9.1, 9.2, 9.3, 9.4, 9.5, 9.6, 9.7, 9.8, 9.9, 10.0, 10.1, 10.2, 10.3, 10.4, or 10.5. The pH of the composition may also be within a range with a lower limit of 8.5, 8.6, 8.7, 8.8, 8.9, 9.0, 9.1, 9.2, 9.3, 9.4, or 9.5. The pH may also be 8.5, 9.0, 9.1, 9.2, 9.3, 9.4, 9.5, 9.6, 9.7, 9.8, 9.9, 10.0, or 10.5. In particular, the pH may be 9.4.

b. Glycol

The glycol may be ethylene glycol, propylene glycol, or diethylene glycol. The glycol concentration may be within a range with an upper limit of 25, 30, 35, 40, 45, 50, 55, or 60% (v/v). The glycol concentration may also be within a range with a lower limit of 20, 25, 30, 35, 40, 45, 50, or 55% (v/v). The concentration of the glycol may be 20, 25, 30, 35, 40, 45, 50, 55, or 60% (v/v). In particular, the glycol concentration may be 50% (v/v).

c. Alcohol

The alcohol may be ethanol, benzyl alcohol or isopropyl alcohol. The alcohol concentration may be within a range with an upper limit of 10, 15, 20, or 25% (v/v). The alcohol concentration may also be within a range with a lower limit of 5, 10, 15, or 20% (v/v). The alcohol concentration may also be 5, 10, 15, 20, or 25% (v/v). In particular, the alcohol concentration may be 10% (v/v).

d. Pentobarbital

The pentobarbital may be a salt of pentobarbital. The salt may be sodium or calcium. The pentobarbital concentration may be within a range with an upper limit of 60, 70, 80, 90, or 100 mg/mL. The pentobarbital concentration may also be within a range with a lower limit of 10, 20, 30, 40, 50, 60, 70, 80, or 90 mg/mL. The pentobarbital concentration may also be 20, 30, 40, 50, 60, 70, 80, 90, or 100 mg/mL. In particular, the pentobarbital concentration may be 50 mg/mL.

e. Administration

The composition may be adapted for parenteral administration, which may be via infusion, injection, or implantation. The injection may be intradermal, subcutaneous, transdermal, intracavernous, intravitreal, intra-articular, intracerebral, intrathecal, epidural, intravenous, intracardiac, intramuscular, intraosseous, or intraperitoneal. In particular, the administration may be intravenous or intramuscular.

3. Methods of Treatment

Provided herein is a method of treating a disease or condition, which may comprise administering the composition to a subject in need thereof. The disease or condition may be pain, anxiety, insomnia, convulsions, coma inducement, intracranial pressure and traumatic brain injuries. The convulsion may be due to status epilepticus, cholera, eclampsia, meningitis, tetanus, and toxic reactions to strychnine or local anesthetics. Also provided herein is a method of sedating a subject, which may comprise administering the composition to a subject in need thereof. Further provided herein is a method of anesthetizing or preanesthetizing a subject, which may comprise administering the composition to a subject in need thereof. The subject may be a mammal, which may be a human.

The present invention has multiple aspects, illustrated by the following non-limiting examples.

EXAMPLE 1

Effect of Glycol in Pentobarbital Formulation on Drug Precipitation and Stability This example demonstrates that a pentobarbital formulation containing 50% glycol is more stable than other formulations, including a formulation that is currently on the market (also referred to as the marketed formulation or approved formulation). In particular, the formulation provided herein has ~50% lower Impurity 1 at relative retention rate (RRT) 0.7, and therefore is therapeutically safer than the marketed formulation, which has 40% propylene glycol. Six formulation development designs of experiments (DOE) were conducted. The first DOE investigated the impact of pH adjustment and different concentrations of propylene glycol and ethyl alcohol on drug product critical quality attributes (CQAs). The second DOE studied the impact of lowering the pH to 8.7 on drug product CQAs. The third DOE looked into the different concentrations of propylene glycol and ethyl alcohol at target pH 9.5 on drug product CQAs. The fourth DOE inspected pH 9.0 on drug product CQAs. The fifth DOE examined the impact of 44% propylene glycol with target pH at 8.9, 9.0 and 9.1 on drug product CQAs. The last DOE explored the impact of antioxidant BHT and sodium sulfite on drug product CQAs.

The approved pentobarbital formulation is shown in the table below.

TABLE 1

| Ingredient | Function | Approved Pentobarbital Formulation |
|---|---|---|
| Pentobarbital Sodium, USP | Active ingredient | 50 mg/mL |
| Propylene Glycol, USP | Solvent vehicle | 40% (v/v) |
| 190 Proof Alcohol, USP, 190 Proof | Preservative | 10% (v/v) |
| Sodium Hydroxide, NF | pH adjustment | pH adjustment |
| Hydrochloric Acid, NF | pH adjustment | pH adjustment |
| Water for Injection, USP | Vehicle | QS to 100% |

Physicochemical properties of 5 approved drug product batches under Long Term Testing (LTT) conditions are summarized in Table 2. The data were taken from U.S. Food and Drug Administration annual reports.

TABLE 2

Physicochemical Characterization of Approved Pentabarbital Formulation with 40% Propylene Glycol

| Lot | Time | Condition | pH | Color | Clarity | Assay (%) | Related Compound at RRT 0.7 (%) | Total Related Compounds (%) | Reference |
|---|---|---|---|---|---|---|---|---|---|
| 562453F | T = 24 months | LTT | 9.4 | Colorless Solution | Clear solution, no visible particles. | 97.8 | 1 | 1 | 2010 Annual report |
|  | T = 36 months | LTT | 9.4 | Colorless Solution | Clear solution, no visible particles. | 97.1 | 1.3 | 1.5 | 2010 Annual report |
| 562653F | T = 24 months | LTT | 9.4 | Colorless Solution | Clear solution, no visible particles. | 97.6 | 1 | 1 | 2010 Annual report |
|  | T = 36 months | LTT | 9.4 | Colorless Solution | Clear solution, no visible particles. | 96.8 | 1.3 | 1.5 | 2010 Annual report |
| 660303F | T = 12 months | LTT | 9.4 | Colorless Solution | Clear solution, no visible particles. | 98.6 | 0.6 | 0.6 | 2010 Annual report |
|  | T = 24 months | LTT | 9.5 | Colorless Solution | Clear solution, no visible particles. | 99.7 | 1 | 1 | 2010 Annual report |
| 761403F | T = 3 Months | LTT | 9.4 | Colorless Solution | Clear solution, no visible particles. | 99.9 | 0.2 | 0.2 | 2009 Annual report |
|  | T = 12 Months | LTT | 9.4 | Colorless Solution | Clear solution, no visible particles. | 99.8 | 0.6 | 0.6 | 2010 Annual report |
|  | T = 24 Months | LTT | 9.4 | Colorless Solution | Clear solution, no visible particles. | 98.8 | 1 | 1 | 2011 Annual report |
| 761353F | T = 12 Months | LTT | 9.5 | Colorless Solution | Clear solution, no visible particles. | 99.7 | 0.6 | 0.6 | 2010 Annual report |

TABLE 2-continued

Physicochemical Characterization of Approved Pentabarbital Formulation with 40% Propylene Glycol

| Lot | Time | Condition | pH | Color | Clarity | Assay (%) | Related Compound at RRT 0.7 (%) | Total Related Compounds (%) | Reference |
|---|---|---|---|---|---|---|---|---|---|
| | T = 24 Months | LTT | 9.4 | Colorless Solution | Clear solution, no visible particles. | 99 | 1 | 1 | 2011 Annual report |

Related Compound 1 at RRT 0.7 grew from 0.2% (T=3M LTT) to 1.3% (T=36 Month LTT) and Total Related Compounds grew from 0.2% (T=3M LTT) to 1.5% (T=36 Month LTT) based on LTT stability data.

a. Formulation Development Study #1—Compounding Conditions Evaluation

In order to evaluate the roles of propylene glycol and alcohol in the formulation, six lab batches were made with different compounding conditions. Physical observations were performed and recorded during compounding. Lab batches DEF003053-A, DEF003053-B, DEF003053-D and DEF003053-E02 were placed on stability at room temperature, 40° C., and 50° C. Only physical observations were performed and recorded during stability study. The stability study lasted for one month. Physical observations are summarized and tabulated as shown in Table 3.

TABLE 3

Lab Batches Physical Observations Summary

| Lot No. | DEF003053-A | DEF003053-B | DEF003053-C | DEF003053-D | DEF003053-E01 | DEF003053-E02 |
|---|---|---|---|---|---|---|
| Formulation | Full Formulation | Full Formulation | Without Propylene Glycol | Without Alcohol | API only | API only |
| pH adjustment | with pH adjustment | No | Yes | Yes | Yes | No |
| Observation during compounding | No Precipitate | No Precipitate | Precipitate Formed | No Precipitate | Precipitate Formed | No Precipitate |
| Observation during Stability Studies | No Precipitate after one month | No Precipitate after one month | N/A | No Precipitate after one month | N/A | Precipitate observed after one month at 50° C. |

Based on the summary table, propylene glycol increases the solubility of pentobarbital and thus plays an important role in the stability of pentobarbital in solution.

b. Formulation Development Study #2—Lower pH Evaluation

Based on Formulation Development Study #1, four more lab batches were made with different concentrations of propylene glycol and ethyl alcohol at target pH 8.70. The purpose of the study was to determine the influence of low pH and different concentrations of propylene glycol and ethyl alcohol on the product quality. Physical observations were recorded during compounding. Lab batch samples were placed on stability at room temperature, 40° C. and 50° C. Only physical observations were performed and recorded during stability. The stability study lasted one month. Physical observations of these lab batches are summarized and tabulated in Table 4.

TABLE 4

Lab Batches Physical Observations Summary

| Lot No. | DEF00305-F | DEF003053-G | DEF003053-H | DEF003053-I |
|---|---|---|---|---|
| Formulation | 40% propylene glycol and 10% alcohol | 45% propylene glycol and 10% alcohol | 40% propylene glycol and 15% alcohol | 50% propylene glycol and 10% alcohol |
| Target pH | 8.7 | 8.7 | 8.7 | 8.7 |
| Observation during compounding | No Precipitate | No Precipitate | No Precipitate | No Precipitate |
| Observation during Stability Studies | Precipitate observed after 1 day * at room temperature | Precipitate observed after one month at room temperature | Precipitate observed after one month at room temperature | Precipitate observed after 5 weeks at room temperature |

*upon addition of 12 ml of propylene glycol, the pentobarbital re-dissolved.

Based on Formulation Development Study #2, it can be concluded that pentobarbital is not stable below pH 8.7. The proper range of pH is critical for this product. Higher concentrations of propylene glycol and alcohol can delay the precipitation from forming, which reconfirms that propylene glycol plays an important role in the stability of this product.

c. Formulation Development Study #3—Target pH 9.5 Evaluation

In order to understand the impact of product quality with different concentrations of propylene glycol and alcohol at the target pH 9.5, four lab batches were made. These batches did not contain any nitrogen overlay after filling due to limitation in the lab. Observations were recorded during compounding. Lab batch samples were placed on stability at room temperature, 40° C., and 50° C. for three months. Both physical observations and analytical test results were performed on these stability samples and are summarized in Table 5 and Table 6.

TABLE 5

Physical Observations Summary During Compounding and Stability Study

| Lot No. | DEF003062-A | DEF003062-B | DEF003062-C | DEF003062-D |
|---|---|---|---|---|
| Formulation | 40% Propylene Glycol and 10% Alcohol | 45% Propylene Glycol and 10% Alcohol | 50% Propylene Glycol and 10% alcohol | 40% Propylene Glycol and 15% Alcohol |
| Target pH | 9.5 | 9.5 | 9.5 | 9.5 |
| Observation during compounding | No Precipitate | No Precipitate | No Precipitate | No Precipitate |
| Observation during Stability Study | No Precipitate after three months | No Precipitate after three months | No Precipitate after three months | No Precipitate after three months |

TABLE 6

Analytical Test Results Summary

| Lot No. | Lot Description | Temperature/Time | Assay % | RRT 0.7 | Total |
|---|---|---|---|---|---|
| DEF003062-A | 40% propylene glycol and 10% alcohol (control) | T = 0 | 99.4 | 0.016 | 0.092 |
| | | 25° C./T = 1 M | 98.0 | 0.05 | 0.14 |
| | | 40° C./T = 1 M | 97.4 | 0.97 | 1.41 |
| | | 50° C./T = 1 M | 96.4 | 0.98 | 1.42 |
| | | 40° C./T = 2.5 M | 93.8 | 1.07 | 2.21 |
| | | 50° C./T = 2.5 M | 90.4 | 0.94 | 2.76 |
| DEF003062-B | 45% propylene glycol and 10% alcohol | T = 0 | 101.5 | 0.016 | 0.091 |
| | | 25° C./T = 1 M | 98.5 | 0.04 | 0.13 |
| | | 40° C./T = 1 M | 96.1 | 0.82 | 1.36 |
| | | 50° C./T = 1 M | 95.0 | 0.77 | 1.41 |
| | | 40° C./T = 2.5 M | 92.5 | 0.88 | 2.15 |
| | | 50° C./T = 2.5 M | 93.3 | 0.86 | 2.17 |
| DEF003062-C | 50% propylene glycol and 10% alcohol | T = 0 | 99.5 | 0.016 | 0.084 |
| | | 25° C./T = 1 M | 99.3 | 0.04 | 0.13 |
| | | 40° C./T = 1 M | 97.6 | 0.65 | 1.13 |
| | | 50° C./T = 1 M | 97.2 | 0.61 | 1.22 |
| | | 40° C./T = 2.5 M | 95.1 | 0.69 | 1.85 |
| | | 50° C./T = 2.5 M | 94.5 | 0.70 | 1.95 |
| DEF003062-D | 40% propylene glycol and 15% alcohol | T = 0 | 101.0 | 0.016 | 0.084 |
| | | 25° C./T = 1 M | 99.2 | 0.05 | 0.13 |
| | | 40° C./T = 1 M | 99.5 | 0.74 | 1.19 |
| | | 50° C./T = 1 M | 93.7 | 0.69 | 1.31 |
| | | 40° C./T = 2.5 M | 96.6 | 0.83 | 2.10 |
| | | 50° C./T = 2.5 M | 93.1 | 0.79 | 2.17 |

Based on the physical and analytical results, the following conclusion can be made:

There was no precipitate observed for these four batches at pH 9.5.

Related Compound 1 at RRT 0.7 can be decreased ~36% with 50% propylene glycol. The decrease in Related Compound 1 at RRT 0.7 was calculated with respect to the control at 40° C. at 2.5 months. Details of that comparison are contained in Table 7.

TABLE 7

Related Compound 1 at RRT 0.7 Results Comparison

| Stability Conditions/Time | Batch No | Lot Description | RRT 0.7 | Decreased % |
|---|---|---|---|---|
| 40° C./T = 2.5 M | DEF003062-A | 40% propylene glycol and 10% alcohol (control) | 1.07 | N/A |
| | DEF003062-B | 45% propylene glycol and 10% alcohol | 0.88 | −17.76% |
| | DEF003062-C | 50% propylene glycol and 10% alcohol | 0.69 | −35.51% |
| | DEF003062-D | 40% propylene glycol and 15% alcohol | 0.83 | −22.43% |

Accordingly, although a pH of 9.5 prevents precipitation, it leads to an increase in Related Compound 1 concentrations at the propylene glycol concentration of the marketed formulation (40%). These results demonstrate that increasing the glycol concentration to 50% (v/v) reduces the amount of Related Compound 1, and therefore the amount of pentobarbital degradation.

d. Formulation Development Study #4—Target pH 9.0 Evaluation

Four lab batches similar to Formulation Development Study #3 were made. The purpose of these batches was to find out if impurity at RRT 0.7 can be reduced by making lab batches with different concentrations of propylene glycol and alcohol at the target pH of 9.0. These batches did not contain any nitrogen layering after filling. These four lab batches were placed on stability at room temperature, 40° C., and 50° C. Both physical observations and analytical tests were performed on these stability samples and are summarized in Table 8 and Table 9.

TABLE 8

Physical Observations Summary (Lot. No. DEF003062)

| Lot No. | DEF003062-F | DEF003062-G | DEF003062-H | DEF003062-E |
|---|---|---|---|---|
| Formulation | 40% propylene glycol and 10% alcohol | 45% propylene glycol and 10% alcohol | 50% propylene glycol and 10% alcohol | 40% propylene glycol and 15% alcohol |
| Target pH | 9.0 | 9.0 | 9.0 | 9.0 |
| Observation during compounding | No Precipitate | No Precipitate | No Precipitate | No Precipitate |
| Observation during Stability Study | Precipitate observed after 2 month at room temperature | Precipitate observed after 3 month at room temperature | No Precipitate observed after 3 month | No Precipitate observed after 3 month |

TABLE 9

Analytical Test Results Summary (Lot. No. DEF003062)

| Lot No. | Description | Temperature/Time | Assay % | RRT 0.7 | Total |
|---|---|---|---|---|---|
| DEF003062E | 40% propylene glycol and 15% alcohol | T = 0 | 101.1 | 0.015 | 0.079 |
| | | 25° C./T=1 M | 98.2 | 0.03 | 0.12 |
| | | 40° C./T=1 M | 95.7 | 0.52 | 0.90 |
| | | 50° C./T=1 M | 94.8 | 0.51 | 1.00 |
| | | 40° C./T = 2.5 M | 94.1 | 0.58 | 1.52 |
| | | 50° C./T = 2.5 M | 95.4 | 0.54 | 1.51 |
| DEF003062F | 40% propylene glycol and 10% alcohol (control) | T = 0 | 102.7 | 0.015 | 0.101 |
| | | 25° C./T = 1 M | 98.8 | 0.04 | 0.13 |
| | | 40° C./T = 1 M | 97.1 | 0.69 | 1.03 |
| | | 50° C./T = 1 M | 96.9 | 0.73 | 1.07 |
| | | 40° C./T = 2.5 M | 95.0 | 0.83 | 1.68 |
| | | 50° C./T = 2.5 M | 94.1 | 0.73 | 1.69 |
| DEF003062G | 45% propylene glycol and 10% alcohol | T = 0 | 99.4 | 0.015 | 0.092 |
| | | 25° C./T = 1 M | 97.3 | 0.03 | 0.12 |
| | | 40° C./T = 1 M | 96.6 | 0.56 | 0.89 |
| | | 50° C./T = 1 M | 96.8 | 0.59 | 0.92 |
| | | 40° C./T = 2.5 M | 93.8 | 0.62 | 1.41 |
| | | 50° C./T = 2.5 M | 94.2 | 0.58 | 1.79 |
| DEF003062H | 50% propylene glycol and 10% alcohol | T = 0 | 99.5 | 0.015 | 0.078 |
| | | 25° C./T = 1 M | 99.0 | 0.02 | 0.11 |
| | | 40° C./T = 1 M | 96.5 | 0.44 | 0.73 |
| | | 50° C./T = 1 M | 97.0 | 0.46 | 0.75 |
| | | 40° C./T = 2.5 M | 95.2 | 0.49 | 1.21 |
| | | 50° C./T = 2.5 M | 95.8 | 0.46 | 1.37 |

Based on the physical and analytical results summary, the following conclusion was made:

Precipitate has been observed on batch DEF003062-F (control) and DEF003062-G (45% PG).

These results indicate that pentobarbital is not stable when the pH is ~9.0 and the propylene glycol concentration is less than 50%. Related Compound 1 at RRT 0.7 can be decreased ~41% with 50% propylene glycol at pH 9.0. The decrease in Related Compound 1 at RRT 0.7 is calculated versus the approved formulation control, lot DEF003062-F in Table 10 and lot DEF003062-A in Table 11.

TABLE 10

Related Compound 1 at RRT 0.7 Comparison Summary (Lot. No. DEF003062E-H)

| Stability Conditions/Time | Batch No | Composition Description | RRT 0.7 | Decreased % |
|---|---|---|---|---|
| 40° C./T = 2.5 M | DEF003062-F | Approved Formulation: 40% propylene glycol and 10% alcohol (control) | 0.83 | N/A |
| | DEF003062-G | with 45% propylene glycol and 10% alcohol | 0.62 | −25.30% |
| | DEF003062-H | with 50% propylene glycol and 10% alcohol | 0.49 | −40.96% |
| | DEF003062-E | with 40% propylene glycol and 15% alcohol | 0.58 | −30.12% |

TABLE 11

Related Compound 1 at RRT 0.7 Comparison Summary (Lot No. DEF003062A-D)

| Stability Conditions/Time | Batch No | Composition Description | RRT 0.7 pH 9.5 | RRT 0.7 pH 9.0 | Decreased % |
|---|---|---|---|---|---|
| 40° C./T = 2.5 M | DEF003062-A | 40% propylene glycol and 10% alcohol (control) | 1.07 | 0.83 | −22.43% |
| | DEF003062-B | 45% propylene glycol and 10% alcohol | 0.88 | 0.62 | −29.55% |
| | DEF003062-C | 50% propylene glycol and 10% alcohol | 0.69 | 0.49 | −28.99% |
| | DEF003062-D | 40% propylene glycol and 15% alcohol | 0.83 | 0.58 | −30.12% |

Accordingly, even at a lower pH of 9.0, glycol at a concentration of 50% (v/v) is capable of preventing pentobarbital precipitation, and reducing the amount of Related Compound 1, and thus pentobarbital degradation.

e. Formulation Development Study #5—44% Propylene Glycol Evaluation

In order to determine at what pH precipitate forms at room temperature, three lab batches were made with 44% propylene glycol and target pH at 9.1, 9.0 and 8.9. There was no precipitate found during compounding. Lab batch samples were placed on stability at room temperature, 40° C., and 50° C. for three months. Only physical observations were performed during the stability study. Physical observations are summarized in Table 12.

TABLE 12

Physical Observations Summary (Lot No. DEF003073A-C)

| Lot No. | DEF003073-A | DEF003073-B | DEF003073-C |
|---|---|---|---|
| Formulation | 44% propylene glycol and 10% alcohol | 44% propylene glycol and 10% alcohol | 44% propylene glycol and 10% alcohol |
| Target pH | 9.1 | 9.0 | 8.9 |
| Observation during compounding | No Precipitate | No Precipitate | No Precipitate |
| Observation during Stability Study | Precipitate found after three months at room temperature and 50° C. | Precipitate found after three months at room temperature and 50° C. | Precipitate found after three months at room temperature and 50° C. |

Conclusion:

Based on the physical observations, pentobarbital is not stable with 44% propylene glycol at pH-9.0.

f. Formulation Development Study #6—Antioxidant Formulation Evaluation

In order to reduce Related Compound 1 at RRT 0.7, five lab batches were made by adding butylated hydroxytoluene (BHT) or sodium sulfite in the formulation. These lab batches contained nitrogen layering after filling. These five lab batches were placed on stability at room temperature and 40° C. There was no precipitate found in these lab batch stability studies. Analytical tests of stability samples were performed and results are summarized in Table 13.

TABLE 13

Antioxidant Evaluation Analytical Test Results Summary

| Formulation | Lot | Time | Condition | Related Compound 1 at RRT ~0.7 (%) | Total Related Compounds (%) |
|---|---|---|---|---|---|
| Liquid Formulation with Sodium Sulfite (1 mg/ml) | DEF003093-D | T = 0 | | 0.01 | 0.11 |
| | | T = 4 Weeks | 25° C. | 0.03 | 0.12 |
| | | T = 3 Weeks | 40° C. | 0.23 | 0.35 |
| | | T = 4 Weeks | 40° C. | 0.30 | 0.40 |
| | | T = 5 Weeks | 40° C. | 0.43 | 0.57 |
| Regular Nembutal Liquid Formulation (control) | DEF026031-A | T = 1 M | 25° C. | 0.04 | 0.12 |
| | | T = 1 M | 40° C. | 0.28 | 0.36 |
| Liquid Formulation with BHT (0.02 mg/ml) | DEF026031-B | T = 1 M | 25° C. | 0.04 | 0.13 |
| | | T = 1 M | 40° C. | 0.26 | 0.35 |
| Liquid Formulation with Sodium Sulfite (1 mg/m1) | DEF026031-C | T = 1 M | 25° C. | 0.03 | 0.14 |
| | | T = 1 M | 40° C. | 0.25 | 0.35 |
| Liquid Formulation with BHT (0.02 mg/ml) | DEF003093-E | T = 0 | | 0.02 | 0.13 |
| | | T = 4 Weeks | 25° C. | 0.02 | 0.12 |
| | | T = 3 Weeks | 40° C. | 0.26 | 0.38 |
| | | T = 4 Weeks | 40° C. | 0.36 | 0.47 |
| | | T = 5 Weeks | 40° C. | 0.41 | 0.54 |

Conclusion:

Based on this stability data, there is no significant difference between antioxidant formulation and regular formulation. Accordingly, an antioxidant may be added to a pentobarbital formulation without affecting the degradation of pentobarbital.

EXAMPLE 2

Stability Testing of Pentobarbital Formulations

This example demonstrates that a pentobarbital formulation provided herein, having 50% glycol at a pH of 9.4, is more stable than the currently-marketed formulation.

Details of Stability Batches are as follow:

Marketed formulation (Pentobarbital Sodium Injection, USP), 50 mg/mL, 50 mL vial Batch Size 200 Liters (206.4 kg)

Fill Volume Target=53.0 mL±2.0 mL

Product Code #686

Exhibit Lot #041143

The stability batch was manufactured using components and the container/closure system identified in the master batch record.

Marketed formulation (Pentobarbital Sodium Injection, USP), 50 mg/mL, 20 mL vial Batch Size 200 Liters (206.4 kg)

Fill Volume Target=21.5 mL±1.0 mL

Product Code #688

Exhibit Lot #041173

The stability batch was manufactured using components and the container/closure system identified in the master batch record.

Manufactured batches were evaluated for formulation, filtration, filling, and hold time for the marketed formulation (Pentobarbital Sodium Injection, USP), 50 mg/mL. Sampling and testing were performed at critical steps within those processes.

The stability study for marketed formulation (Pentobarbital Sodium Injection, USP), 50 mg/mL were conducted according to the standard stability protocols:

For Code#686: stability protocol #18-1-686R-13

For Code#688: stability protocol #18-1-688R-13 at the following ICH Guideline conditions:

Long Term Testing (LTT): 25°±2° C./60%±5% Relative Humidity

Accelerated Testing (ACC): 40°±2° C./75%±5% Relative Humidity

Respective results are summarized in FIGS. 1-8.

A comparison of the physical attributes of the marketed pentobarbital formulation and the improved formulation provided herein is shown in Table 14.

TABLE 14

ACC Stability Data Comparison Between Approved Formulation Product with 40% Propylene Glycol and Proposed Formulation with 50% Propylene Glycol

| Lot | Time | Condition | Assay (%) | Largest Unidentified Individual Related Compound | Related Compound at RRT 0.7 (%) | Total Related Compounds (%) | pH | Product Appearance |
|---|---|---|---|---|---|---|---|---|
| 041143 | T = 0 | | 100.4 | LT 0.1 | LT 0.1 | 0.1 | 9.5 | Conforms |
| (50 mL) | T = 1M | 40° C. | 99.2 | LT 0.1 | 0.2 | 0.3 | 9.4 | Conforms |
| Code# 686 | T = 2M | 40° C. | 98.1 | LT 0.1 | 0.4 | 0.5 | 9.4 | Conforms |
| | T = 3M | 40° C. | 100.2 | LT 0.1 | 0.6 | 0.7 | 9.4 | Conforms |
| 080053F | T = 0 | | 101.2 | LT 0.1 | LT 0.1 | LT 0.1 | 9.4 | Conforms |
| (20 mL) | T = 1M | 40° C. | 99.5 | 0.1 | 0.7 | 0.8 | 9.4 | Conforms |
| Approved | T = 2M | 40° C. | 99.3 | LT 0.1 | 0.9 | 1.0 | 9.4 | Conforms |
| Formulation | T = 3M | 40° C. | 99.5 | 0.1 | 1.1 | 1.3 | 9.4 | Conforms |
| 041173 | T = 0 | | 99.9 | LT 0.1 | LT 0.1 | 0.1 | 9.5 | Conforms |
| (20 mL) | T = 1M | 40° C. | 99.4 | LT 0.1 | 0.2 | 0.3 | 9.4 | Conforms |

TABLE 14-continued

ACC Stability Data Comparison Between Approved Formulation Product with 40% Propylene Glycol and Proposed Formulation with 50% Propylene Glycol

| Lot | Time | Condition | Assay (%) | Largest Unidentified Individual Related Compound | Related Compound at RRT 0.7 (%) | Total Related Compounds (%) | pH | Product Appearance |
|---|---|---|---|---|---|---|---|---|
| Code# 688 | T = 2M | 40° C. | 99.2 | Not detected | 0.4 | 0.5 | 9.4 | Conforms |
|  | T = 3M | 40° C. | 98.6 | LT 0.1 | 0.6 | 0.7 | 9.4 | Conforms |
| 080103 | T = 0 |  | 99.4 | LT 0.1 | LT 0.1 | LT 0.1 | Conforms | Conforms |
| (50 mL) | T = 1M | 40° C. | 98.6 | 0.1 | 0.7 | 0.8 | 9.5 | Conforms |
| Approved | T = 2M | 40° C. | 96.7 | 0.1 | 0.9 | 1.0 | 9.4 | Conforms |
| Formulation | T = 3M | 40° C. | 98.8 | 0.1 | 1.1 | 1.3 | 9.4 | Conforms |
|  | Specification |  | 92.0 to 108.0% | NMT 0.2% | NMT 1.0 | NMT 1.5% | 9.0 to 10.5 | Clear colorless Solution |

Both the approved formulation product with 40% propylene glycol and proposed formulation with 50% propylene glycol samples were placed into ACC stability study and tested under the same conditions and time points.

Based on ACC T=3M stability data, pentobarbital Related Compound 1 at RRT 0.7 of the improved formulation (0.6%) has been reduced to ~45% less than the approved formulation product and Total Related Compounds of the improved formulation (0.7%) has been reduced to ~46% less than the approved formulation product.

The formulations of Code 688 and 686 are shown in the tables below.

TABLE 15

Code: 688 (20 mL fill/20 cc vial)

| Ingredient | Unit Composition (mg/mL) |
|---|---|
| Pentobarbital Sodium, USP | 50 mg/mL |
| Propylene Glycol, USP | 50% (v/v) (518.8 mg/mL) |
| Alcohol, USP, 190 Proof | 10% (v/v) (90.72 mg/mL) |
| Sodium Hydroxide, NF | pH adjustment |
| Hydrochloric Acid, NF | pH adjustment |
| Activated Charcoal, USP* | 0.125 mg/mL |
| Nitrogen, NF | QS |
| Water for Injection, USP | QS to 100% |

*Removed during compounding process.

TABLE 16

Code: 686 (50 mL fill/50 cc vial)

| Ingredient | Unit Composition (mg/mL) |
|---|---|
| Pentobarbital Sodium, USP | 50 mg/mL |
| Propylene Glycol, USP | 50% (v/v) (518.8 mg/mL) |
| Alcohol, USP, 190 Proof | 10% (v/v) (90.72 mg/mL) |
| Sodium Hydroxide, NF | pH adjustment |
| Hydrochloric Acid, NF | pH adjustment |
| Activated Charcoal, USP* | 0.125 mg/mL |
| Nitrogen, NF | QS |
| Water for Injection, USP | QS to 100% |

*Removed during compounding process.

Accordingly, pentobarbital degradation, and the accumulation of potentially toxic degradation products, can be reduced in comparison to the marketed formulation by using 50% propylene glycol at a pH of 9.4 in a pentobarbital formulation.

The invention claimed is:

1. A composition comprising 50 mg/mL of a pentobarbital, 50% (v/v) propylene glycol, 10% (v/v) ethanol, and water, wherein the pH of the composition is 9.0-9.5.

2. The composition of claim 1, wherein the pentobarbital is a sodium or calcium salt of pentobarbital.

3. The composition of claim 2, wherein the pentobarbital is a sodium salt of pentobarbital.

4. The composition of claim 1, wherein the pH is 9.4.

* * * * *